United States Patent
Pan et al.

(10) Patent No.: US 10,011,819 B2
(45) Date of Patent: Jul. 3, 2018

(54) CULTURE MEDIUM FOR PREPARING NEURAL STEM CELLS AND USE THEREOF

(71) Applicant: Guangzhou Institutes of Biomedicine and Health, Chinese Academy of Sciences, Guangzhou (CN)

(72) Inventors: Guangjin Pan, Guangzhou (CN); Duanqing Pei, Guangzhou (CN); Lihui Wang, Guangzhou (CN); Linli Wang, Guangzhou (CN); Yanting Xue, Guangzhou (CN)

(73) Assignee: GUANGZHOU INSTITUTES OF BIOMEDICINE AND HEALTH, CHINESE ACADEMY OF SCIENCES, Guangzhou (CN)

( * ) Notice: Subject to any disclaimer, the term of this patent is extended or adjusted under 35 U.S.C. 154(b) by 372 days.

(21) Appl. No.: 14/382,188

(22) PCT Filed: Feb. 6, 2013

(86) PCT No.: PCT/CN2013/071468
§ 371 (c)(1),
(2) Date: Aug. 29, 2014

(87) PCT Pub. No.: WO2013/127293
PCT Pub. Date: Sep. 6, 2013

(65) Prior Publication Data
US 2015/0030570 A1    Jan. 29, 2015

(30) Foreign Application Priority Data
Feb. 29, 2012    (CN) .......................... 2012 1 0051095

(51) Int. Cl.
*C12N 5/0797* (2010.01)
*A61K 35/30* (2015.01)
*C12N 15/85* (2006.01)

(52) U.S. Cl.
CPC ............ *C12N 5/0623* (2013.01); *A61K 35/30* (2013.01); *C12N 15/85* (2013.01); *C12N 2501/15* (2013.01); *C12N 2501/155* (2013.01); *C12N 2501/727* (2013.01); *C12N 2501/999* (2013.01); *C12N 2506/25* (2013.01)

(58) Field of Classification Search
CPC ....... C12N 5/0623; C12N 15/85; A61K 35/30
USPC ........ 424/93.7; 435/404, 377, 455, 446, 325
See application file for complete search history.

(56) References Cited

U.S. PATENT DOCUMENTS

| | | | |
|---|---|---|---|
| 8,765,470 B2 * | 7/2014 | Thomson | C12N 5/0696 435/377 |
| 2010/0111914 A1 | 5/2010 | Zhang et al. | |
| 2012/0058562 A1 * | 3/2012 | Thomson | C12N 5/0696 435/455 |
| 2012/0220034 A1 * | 8/2012 | Ahlfors | C12N 5/0618 435/375 |

FOREIGN PATENT DOCUMENTS

| | | | |
|---|---|---|---|
| CN | 102191221 A1 | 9/2011 | |
| CN | 102604894 A | 7/2012 | |
| JP | 2002-518990 A | 7/2002 | |
| JP | 2007-174954 A | 7/2007 | |
| WO | 2009006422 A1 | 1/2009 | |
| WO | 2010063848 A1 | 6/2010 | |
| WO | 2010144696 A1 | 12/2010 | |
| WO | 20110019092 A1 | 2/2011 | |
| WO | WO 2011047300 A1 * | 4/2011 | ........... C12N 5/0696 |
| WO | 2011056971 A2 | 5/2011 | |
| WO | 20110060100 A1 | 5/2011 | |
| WO | WO 2011050476 A1 * | 5/2011 | ........... C12N 5/0618 |
| WO | WO 2011056971 A2 * | 5/2011 | ........... A61K 35/545 |
| WO | 2012022725 A2 | 2/2012 | |
| WO | 20120022725 A2 | 2/2012 | |
| WO | 2012034101 A2 | 3/2012 | |

OTHER PUBLICATIONS

Lee (Human Sensory Neurons Derived from Induced Pluripotent Stem Cells Support Varicella-Zoster Virus Infection, 2012).*
Neely (DMH1, a Highly Selective Small Molecule BMP Inhibitor Promotes Neurogenesis of hiPSCs: Comparison of PAX6 and SOX1 Expression during Neural Induction, 2012).*
Feng Nianhua et al., Differentiation of human induced pluripotent stem cells into neural cells, Chinese Journal of Pathophysiology, ISSN 1000-4718, vol. 26, No. 8, pp. 1662-1664, 2010, see abstract.
Ji Xudong et al., Investigation of differentiation derived from human umbilical cord blood into neuron-like cells, Henan Medical Research, ISSN 1004-437X, vol. 14, No. 3, pp. 215-219, Sep. 2005.
Wenlin Li et al., Generation of rat and human induced pluripotent stem cells by combining Genetic reprogramminga nd chemical inhibitor, Cell Stem Cell, vol. 4.
Feng Nianhua et al., Differentiation of induced pluripotent stem cells into neural stem cells, Basic & Clinical Medicine, ISSN 1001-6325, vol. 30, No. 12, pp. 1263-1267, Dec. 2010.
International Search Report and Written Opinion for PCT/CN2013/071468; dated May 26, 2013.
Office Action issued in related Canadian patent application No. 2865817, dated Oct. 19, 2015.
Response to Office Action filed in related Canadian patent application No. 2865817, dated Apr. 1, 2016.
Office Action issued in related Chinese patent application No. 201210051095.0, dated Jan. 14, 2013.

(Continued)

*Primary Examiner* — Scott Long
*Assistant Examiner* — Nghi V Nguyen
(74) *Attorney, Agent, or Firm* — Westman, Champlin & Koehler, P.A.; Z. Peter Sawicki; Amanda M. Prose (57) ABSTRACT

Provided are a culture medium for preparing neural stem cell and use thereof, the culture medium for preparing neural stem cell comprising: a basic culture medium suitable for the growth of stem cell, and a cell signal pathway inhibitor selected from at least one of GSK inhibitor, MEK inhibitor, TGF-β inhibitor, ROCK inhibitor and BMP inhibitor.

5 Claims, 5 Drawing Sheets

(56) References Cited

OTHER PUBLICATIONS

Office Action issued in related Chinese patent application No. 201210051095.0, dated Jul. 3, 2013.
Office Action issued in related Chinese patent application No. 201210051095.0, dated Dec. 5, 2013.
Notice of Allowance issued in related Chinese patent application No. 201210051095.0, dated May 12, 2014.
Granted CN Pat. No. ZL201210051095.0 issued from related Chinese patent application No. 201210051095.0, dated Jul. 30, 2014; English translation of granted claims.
Extended European Search Report issued in related European patent application No. 13754150.4, dated Jul. 22, 2015.
Li, X., et al., (2008) "ROCK inhibitor improves survival of cryopreserved serum/feeder-free single human embryonic stem cells", Human Reproduction, vol. 24, No. 3, 580-589.
Wang, L., et al., (2013) "Generation of integration-free neural progenitor cells from cells in human urine", Nature Methods, vol. 10, No. 1, 84-89.
Pankratz, M.T., et al (2007) "Directed Neural Differentiation of Human Embryonic Stem Cells via an Obligated Primitive Anterior Stage" vol. 25, No. 6, 1511-1520.
Zhou, T., et al. (2011) "Generation of induced pluripotent stem cells from urine" Journal of the American Society of Nephrology, vol. 22, No. 7, 1221-1228.
Further Communication issued in related European patent application No. 13754150.4, dated Jan. 7, 2016.
Response to Office Action filed in related European patent application No. 13754150.4, dated Jan. 13, 2016.
Office Action issued in related Japanese patent application No. 2014-559070, dated Sep. 20, 2016.
Office Action issued in related Japanese patent application No. 2014-559070, dated Jan. 5, 2016.
Hao, J., et al., (2010) "In Vivo Structure—Activity Relationship Study of Dorsomorphin Analogues Identifies Selective VEGF and BMP Inhibitors" ASC Chemical Biology, vol. 5, No. 2, 245-253.
Office Action issued in related Korean patent application No. 10-2014-7026996, dated Feb. 29, 2016.
Kim, J.B., et al., (2009) "Oct4-Induced Pluripotency in Adult Neural Stem Cells" Cell 136, 411-419.
Decision to Grant a Patent issued in related Korean patent application No. 10-2014-7026996, dated Sep. 21, 2016.
Decision to Grant a Patent issued in related Japanese patent application No. 2014-559070, dated Jan. 10, 2017.

* cited by examiner

CULTURE MEDIUM FOR PREPARING NEURAL STEM CELLS AND USE THEREOF

CROSS-REFERENCE TO RELATED APPLICATIONS

This application is a Section 371 National Stage Application of International Application No. PCT/CN2013/071468, filed Feb. 6, 2013, and published as WO2013/127293 on Sep. 6, 2013, in Chinese, which claims priority and benefits of Chinese Patent Application No. 201210051095.0, filed with State Intellectual Property Office on Feb. 29, 2012, the entire contents of which are incorporated herein by reference.

TECHNICAL FIELD

Embodiments of the present disclosure generally relate to a field of biomedicine, more particularly, to a medium for preparing a neural stem cell and use thereof.

BACKGROUND

Stem cell is an initial source of human and various tissues and cells thereof, of which the most prominent biological characteristic is not only possessing a probability of self-renewal and proliferation, but also possessing a probability of pluripotency. The stem cells are classified into somatic stem cells and embryonic stem (ES) cells according to different sources. The somatic stem cells include neural stem cells, mesenchymal stem cells, and hemopoietic stem cells, etc. Currently, besides many studies on the hemopoietic stem cells and the mesenchymal stem cells, researches on the neural stem cells are also relative deep.

In 1992, Reynolds and Weiss et al. firstly isolated neural stem cells from a corpus striatum of an adult mouse, which not only possess probabilities of self-renewal, division and proliferation, but also may differentiate to most types of cells of nervous system, which may respond to damage and disease. In 1998, Okano from Japan and Goldman from Cornell university co-demonstrated that a presence of the neural stem cells in tissues of human adult brain. Currently, it has been demonstrated the presence of multipotent stem cells in nervous system through gradually practice, then has been successfully isolated therefrom, which brings new hopes for repair of nervous system damage and cell replacement therapy of neurodegenerative disorders. As a characteristic of a neuron being non-regenerative and non-self-repairing has been an insurmountable obstacle in medical science, and due to vulnerability of organization structure of central nervous system and importance thereof on intellectual activity, further central nervous system disorder and sequela thereof are one of the most chronic diseases affecting human health and quality of life, thereof study on neural stem cells has become a most hot topic and focused part in a field of stem cells research, which has a bright prospect in clinical application.

However, currently the research related to neural stem cells still needs to be improved.

SUMMARY

Embodiments of the present disclosure seek to solve at least one of the problems existing in the related art to at least some extent. Thus, one purpose of the present disclosure is to provide means for preparing a neural stem cell effectively.

Embodiments of a first broad aspect of the present disclosure provide a medium for preparing a neural stem cell. According to embodiments of the present disclosure, the medium may comprise: a basic medium for culturing a stem cell, and an inhibitor being at least one selected from a group consisting of GSK inhibitor, MEK inhibitor, TGF-β inhibitor, ROCK inhibitor and BMP inhibitor. Inventors of the present disclosure find out that using the medium to culture somatic cells, particularly somatic cells expressing transcriptional regulation factors, may effectively transdifferentiate the somatic cells to neural stem cells (herein also known as "induced neural stem cell"), which may greatly shorten times for transdifferentiation.

Embodiments of a second broad aspect of the present disclosure provide a kit for preparing a neural stem cell. According to embodiments of the present disclosure, the kit may comprise: an inhibitor being at least one selected from a group consisting of GSK inhibitor, MEK inhibitor, TGF-β inhibitor; ROCK inhibitor and BMP inhibitor. Inventors of the present disclosure find out that using the kit to culture somatic cells, particularly somatic cells expressing transcriptional regulation factors, may effectively transdifferentiate the somatic cells to neural stem cells, which may greatly shorten times for transdifferentiation.

Embodiments of a third broad aspect of the present disclosure provide a kit for preparing a neural stem cell, the kit may include the medium above-mentioned. Inventors of the present disclosure find out that using the kit to culture somatic cells, particularly somatic cells expressing transcriptional regulation factors, may effectively transdifferentiate the somatic cells to neural stem cells, which may greatly shorten times for transdifferentiation.

Embodiments of a fourth broad aspect of the present disclosure provide use of the kit above-mentioned in the preparation of a neural stem cell. Using the kit according to embodiments of the present disclosure, may effectively culture the somatic cells, particularly somatic cells expressing transcriptional regulation factors, which may further effectively transdifferentiate the somatic cells to neural stem cells with greatly-shortened time.

Embodiments of a fifth broad aspect of the present disclosure provide use of the medium above-mentioned in the preparation of a neural stem cell, which may effectively transdifferentiate the somatic cells to neural stem cells with greatly-shortened time by means of culturing the somatic cells in vitro, particularly somatic cells expressing transcriptional regulation factors.

Embodiments of a sixth broad aspect of the present disclosure provide a method of preparing a neural stem cell. According to embodiments of the present disclosure, the method comprises: culturing a somatic cell using the medium above-mentioned, wherein the somatic cell comprises a nucleic acid sequence encoding a pluripotent stem cell factor to induce a transdifferentiation from the somatic cell to the neural stem cell, with the pluripotent stem cell factor being at least one selected from a group consisting of Oct4, Sox2, Klf4 and miR302. Inventors of the present disclosure find out that using the medium according to embodiments of the present disclosure to culture the somatic cell carrying the nucleic acid sequence of the pluripotent stem cell factor coded by specific transcriptional factors, may effectively transdifferentiate the somatic cells to neural stem cells with greatly-shortened time.

Embodiments of a seventh broad aspect of the present disclosure provide a neural stem cell or a derivative thereof. According to embodiments of the present disclosure, the neural stem cell is obtained by the method above-mentioned.

In addition, the neural stem cells or the derivative thereof according to embodiments of the present disclosure may effectively differentiate to neural cells under an appropriate condition.

Embodiments of an eighth broad aspect of the present disclosure provide use of the neural stem cell or the derivative thereof above-mentioned in the preparation of a medicament for treating a disease induced by neural cell damage. As the neural stem cell and the derivative thereof according to embodiments of the present disclosure may effectively differentiate to neural cells under an appropriate condition, then the neural stem cell and the derivative thereof may be further prepared into a medicament, which may be used for treating the disease induced by neural cell damage.

Embodiments of a ninth broad aspect of the present disclosure provide a method of treating a disease induced by neural cell damage. According to embodiments of the present disclosure, the method may comprise: introducing the neural stem cell or the derivative thereof above-mentioned into a patient. By introducing the neural stem cell or the derivative thereof above-mentioned into the patient, the neural stem cells may effectively differentiate to neural cells, which may further remedy a body damage induced by neural cell damage.

Embodiments of a tenth broad aspect of the present disclosure provide a method of preparing a neural stem cell. According to embodiments of the present disclosure, the method may comprise: culturing the neural stem cell above-mentioned under a condition suitable for differentiation. Using the method according to embodiments of the present disclosure, may effectively differentiate the neural stem cells to neural cell, which may effectively prepare the neural cells.

Embodiments of an eleventh broad aspect of the present disclosure provide a system for preparing a neural stem cell. According to embodiments of the present disclosure, the system may comprise: isolating apparatus, for isolating a human urine exfoliative cell from human urine, transforming apparatus, connected to the isolating apparatus, and equipped with a vector of a nucleic acid sequence encoding a pluripotent stem cell factor to transform the human urine exfoliative cell, with the pluripotent stem cell factor being at least one selected from a group consisting of Oct4, Sox2, Klf4 and miR302; and transdifferentiation apparatus, connected to the transforming apparatus, and equipped with the medium above-mentioned, for subjecting transformed human urine exfoliative cell to transdifferentiation, to induce transdifferentiating the transformed human urine exfoliative to the neural stem cell. Using the system may effectively implement the method of the preparing the neural cell above-mentioned, which may effectively prepare the neural stem cells.

Embodiments of a twelfth broad aspect of the present disclosure provide a method of screening a compound for inducing differentiation of a neural stem cell. According to embodiments of the present disclosure, the method may comprise: contacting the neural stem cell above-mentioned with a candidate compound, and determining pluripotency of the neural stem cell prior to and after the step of contacting the neural stem cell with the candidate compound, respectively, wherein the decrease of the pluripotency after contacting the neural stem cell with the candidate compound is an indicator of the candidate compound having the ability of inducing differentiation of a neural stem cell. Using the method may effectively screen to obtain the compound for inducing differentiation of the neural stem cell.

Embodiments of a thirteenth broad aspect of the present disclosure provide a method of treating a neurodegenerative disease or a disease induced by neural cell damage. According to embodiments of the present disclosure, the method may comprise: isolating a somatic cell from a patient; preparing a neural stem cell based on the somatic cell according to the method above-mentioned; and introducing the neural stem cell into the patient. Using the method of treating a neurodegenerative disease or a disease induced by neural cell damage, may effectively introduce obtained neural stem cells into a patient, which may further effectively differentiate to neural cells in the patient, and remedy a body damage induced by neurodegeneration and neural cell damage, which may be able to treat the neurodegenerative disease and the disease induced by neural cell damage.

Embodiments of a fourteenth broad aspect of the present disclosure provide a method of determining whether a medicament affects a nervous system. According to embodiments of the present disclosure, the method may comprise: contacting the medicament with the neural stem cell according to embodiments of the present disclosure, and determining the neural stem cell prior to and after the step of contacting the medicament with the neural stem cell, determining whether the medicament affects the nervous system based on a change of the neural stem cell. Using the method may effectively determine whether the medicament affects the nervous system.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference the accompanying drawings, in which.

DETAILED DESCRIPTION

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

Embodiments of a first broad aspect of the present disclosure provide a medium for preparing a neural stem cell. According to embodiments of the present disclosure, the medium may comprise: a basic medium for culturing a stem cell, and an inhibitor being at least one selected from a group consisting of GSK inhibitor, MEK inhibitor, TGF-β inhibitor; ROCK inhibitor and BMP inhibitor. Inventors of the present disclosure find out that using the medium to culture somatic cells, particularly somatic cells expressing transcriptional regulation factors, may effectively transdifferentiate the somatic cells to neural stem cells, which may greatly shorten times for transdifferentiation.

According to embodiments of the present disclosure, types of the basic medium are not subjected to special restrictions. According to an embodiment of the present disclosure, the basic medium is mTeSR1 (may be purchased from Stem Cell company). According to embodiments of the present disclosure, types of the inhibitor are also not subjected to special restrictions, which may be various types of cell signaling pathway inhibitor. According to an embodiment of the present disclosure, the inhibitor may comprise GSK inhibitor CHIR99021, MEK inhibitor PD0325901, TGF-β inhibitor A83-01, ROCK inhibitor thiazovivin and BMP inhibitor DMH1. All of these inhibitors are commercially available, which may further improve efficiency of differentiating the somatic cells to the neural stem cells. Concentrations of each of the inhibitors in the medium for preparing the neural stem cell are not subjected to special restrictions. According to an embodiment of the present disclosure, the inhibitor may comprise: about 0.3 μM to about 30 μM of GSK inhibitor CHIR99021; about 10 nm to about 10 μM of MEK inhibitor PD0325901; about 50 nm to about 5 μM of TGF-β inhibitor A83-01; about 50 nm to about 5 μM of ROCK inhibitor thiazovivin; and about 20 nm to about 2 μM of BMP inhibitor DMH1. Preferably, according to an embodiment of the present disclosure, the inhibitor may comprise: about 3 μM of GSK inhibitor CHIR99021, about 1 μM of MEK inhibitor PD0325901, about 0.5 μM of TGF-β inhibitor A83-01, about 0.5 μM of ROCK inhibitor thiazovivin, and about 0.2 μM of BMP inhibitor DMH1, by which efficiency of differentiating the somatic cells to neural stem cell may be further improved.

Embodiments of a second broad aspect of the present disclosure provide a kit for preparing a neural stem cell. According to embodiments of the present disclosure, the kit may comprise: an inhibitor being at least one selected from a group consisting of GSK inhibitor, MEK inhibitor, TGF-β inhibitor; ROCK inhibitor and BMP inhibitor. Inventors of the present disclosure find out that using the kit to culture somatic cells, particularly somatic cells expressing transcriptional regulation factors, may effectively transdifferentiate the somatic cells to neural stem cells, which may greatly shorten times for transdifferentiation. According to embodiments of the present disclosure, types of the inhibitor are not subjected to special restrictions. According to an embodiment of the present disclosure, the inhibitor may comprise GSK inhibitor CHIR99021, MEK inhibitor PD0325901, TGF-β inhibitor A83-01, ROCK inhibitor thiazovivin and BMP inhibitor DMH1. All of these inhibitors are commercially available, which may further improve efficiency of differentiating the somatic cells to the neural stem cells. Concentrations of each of the inhibitors in the medium for preparing the neural stem cell is not subjected to special restriction. According to an embodiment of the present disclosure, the GSK inhibitor CHIR99021, the MEK inhibitor PD0325901, the TGF-β inhibitor A83-01, the ROCK inhibitor thiazovivin and the BMP inhibitor DMH1 are contained in different containers respectively. Thus, the kit may be conveniently used in transdifferentiating the somatic cells to the neural stem cells. According to an embodiment of the present disclosure, the kit may further comprise a basic medium, wherein the basic medium is mTeSR1 (may be purchased from Stem Cell company).

According to embodiments of the present disclosure, presence of the inhibitor is not subjected to special restriction. According to an embodiment of the present disclosure, in the kit, the inhibitor is dissolved in the basic medium. Thus, the kit may be conveniently used in transdifferentiating the somatic cells to the neural stem cells. According to an embodiment of the present disclosure, in the kit, the inhibitor dissolved in the basic medium may comprise GSK inhibitor CHIR99021 having a concentration of about 3 μM, MEK inhibitor PD0325901 having a concentration of about 1 μM, TGF-β inhibitor A83-01 having a concentration of about 0.5 μM, ROCK inhibitor thiazovivin having a concentration of about 0.5 μM; and BMP inhibitor DMH1 having a concentration of about 0.2 μM. Thus, efficiency of the transdifferentiating the somatic cells to the neural stem cells using the kit above-mentioned may be further improved.

Embodiments of a third broad aspect of the present disclosure provide a kit for preparing a neural stem cell, the kit may include the medium. Inventors of the present disclosure find out that using the kit to culture somatic cells, particularly somatic cells expressing transcriptional regulation factors, may effectively transdifferentiate the somatic cells to neural stem cells, which may greatly shorten times for transdifferentiation. The medium for preparing the neural stem cell has been detailed described above, which is omitted for brevity. Embodiments of a fourth broad aspect of the present disclosure provide use of the kit above-mentioned in the preparation of a neural stem cell. Using the kit according to embodiments of the present disclosure, may effectively culture the somatic cells, particularly somatic cells expressing transcriptional regulation factors, which may further effectively transdifferentiate the somatic cells to neural stem cells with greatly-shortened time. The kit has been detailed described above, which is omitted for brevity. Embodiments of a fifth broad aspect of the present disclosure provide use of the medium above-mentioned in the preparation of a neural stem cell, which may effectively transdifferentiate the somatic cells to neural stem cells with greatly-shortened time by means of culturing the somatic cells in vitro, particularly somatic cells expressing transcriptional regulation factors. The medium for preparing the neural stem cell has been detailed described above, which is omitted for brevity.

Embodiments of a sixth broad aspect of the present disclosure provide a method of preparing a neural stem cell. According to embodiments of the present disclosure, the method may comprise: culturing a somatic cell using the medium above-mentioned, wherein the somatic cell comprises a nucleic acid sequence encoding a pluripotent stem cell factor to induce transdifferentiation from the somatic cell to the neural stem cell, with the pluripotent stem cell factor being at least one selected from a group consisting of Oct4, Sox2, Klf4 and miR302. Inventors of the present disclosure find out that using the medium according to embodiments of the present disclosure to culture the somatic cell carrying the nucleic acid sequence of the pluripotent stem cell factor coded by specific transcriptional factors, may effectively transdifferentiate the somatic cells to neural stem cells with greatly-shortened time. According to embodiments of the present disclosure, types of the somatic cell are not subjected to special restrictions. According to an embodiment of the present disclosure, the somatic cell is a human urine exfoliative cell. Thus, an initial cells may be conveniently obtained, which may further improve efficiency of preparing the neural stem cells, reduce costs for preparing the neural stem cell, and save manpower and material costs for obtaining the initial cells using invasive surgery.

Furthermore, according to embodiments of the present disclosure, the somatic cell comprises a nucleic acid sequence encoding a pluripotent stem cell factor, in which the pluripotent stem cell factor is at least one selected from a group consisting of Oct4, Sox2, Klf4 and miR302, may also be obtained by subjecting somatic cell without the pluripotent stem cell factor to biological treatment. Specifically, according to embodiments of the present disclosure, the somatic cell comprising the nucleic acid sequence encoding the pluripotent stem cell factor, in which the pluripotent stem cell factor is at least one selected from a group consisting of Oct4, Sox2, Klf4 and miR302, may be obtained by following steps:

firstly, centrifuging human urine, to obtain a precipitate, secondly, culturing the precipitate using a medium for culturing urine, to obtain a primary human urine exfoliative cell, and finally, transforming the primary human urine exfoliative cell, using a vector carrying a nucleic acid sequence encoding a pluripotent stem cell factor to obtain the somatic cell, in which the pluripotent stem cell factor is at least one selected from a group consisting of Oct4, Sox2, Klf4 and miR302. According to an embodiment of the present disclosure, the vector carries the nucleic acid sequence encoding Oct4, Sox2, Klf4 and miR302. According to an embodiment of the present disclosure, the vector comprises plasmids carrying the nucleic acid sequence encoding Oct4, Sox2, Klf4 and miR302 respectively. According to an embodiment of the present disclosure, the primary human urine exfoliative cell is transformed by means of electrical transduction.

After obtaining the neural stem cell, the neural stem cell may be further subjected to proliferative culture. According to embodiments of the present disclosure, methods of subjecting the neural stem cell to the proliferative culture are not subjected to special restrictions, according to an embodiment of the present disclosure, the method of preparing the neural stem cell may further comprise following steps to subject the neural stem cell to the proliferative culture:

firstly, pre-culturing the neural stem cell using a basic medium, to obtain an adherent neural stem cell, in which the basic medium may be mTeSR1.

secondly, culturing the adherent neural stem cell in a medium for neural stem cell, in which the medium for neural stem cell comprises DMEM/F2 medium supplemented with about 1% N2 supplement, about 1% non-essential amino acid, about 0.1% heparin, about 20 ng/ml basic fibroblast growth factor and about 20 ng/ml epidermal growth factor.

Embodiments of a seventh broad aspect of the present disclosure provide a neural stem cell or a derivative thereof. According to embodiments of the present disclosure, the neural stem cell is obtained by the method above-mentioned. In addition, the neural stem cells or the derivative thereof according to embodiments of the present disclosure may effectively differentiate to neural cells under an appropriate condition. Embodiments of an eighth broad aspect of the present disclosure provide use of the neural stem cell or a derivative thereof above-mentioned in the preparation of a medicament for treating a disease induced by neural cell damage. As the neural stem cell and the derivative thereof according to embodiments of the present disclosure may effectively differentiate to neural cells under an appropriate condition, then the neural stem cell and the derivative thereof may be further prepared into a medicament, which may be used for treating the disease induced by neural cell damage. Embodiments of a ninth broad aspect of the present disclosure provide a method of treating a disease induced by neural cell damage. According to embodiments of the present disclosure, the method may comprise: introducing the neural stem cell or the derivative thereof above-mentioned into a patient. By introducing the neural stem cell or the derivative thereof above-mentioned into the patient, the neural stem cells may effectively differentiate to neural cells, which may further remedy a body damage induced by neural cell damage.

Embodiments of a tenth broad aspect of the present disclosure provide a method of preparing a neural stem cell. According to embodiments of the present disclosure, the method may comprise: culturing the neural stem cell above-mentioned under a condition suitable for differentiation. Using the method according to embodiments of the present disclosure, may effectively differentiate the neural stem cells to neural cell, which may effectively prepare the neural cells. According to embodiments of the present disclosure, methods of subjecting the neural stem cell to differential culture are not subjected to special restrictions. According to an embodiment of the present disclosure, the neural stem cell is cultured in DMEM/F12 medium supplemented with about 1% N2 supplement, about 1% non-essential amino acid, about 0.1% heparin and neurotrophin, to obtain different types of a neuron and a neuroglia cell, in which the neurotrophin consists of about 10 ng/mL BDNF, about 10 ng/mL GDNF, about 10 ng/mL CNTC and about 10 ng/mL IGF.

Figure 1:
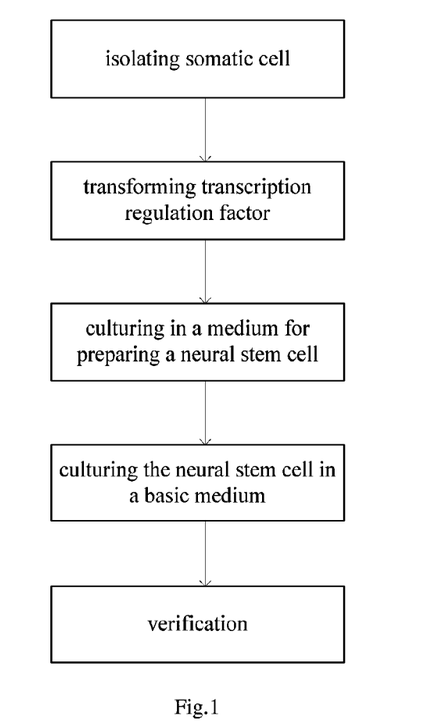
FIG. 1 is a flow chart showing a method of preparing a neural stem cell according to an embodiment of the present disclosure.
Figure 2:
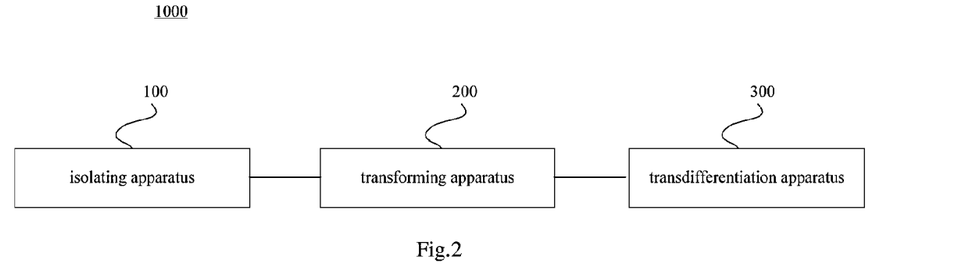
FIG. 2 is a schematic diagram showing a system of preparing a neural stem cell according to an embodiment of the present disclosure.
Figure 3:
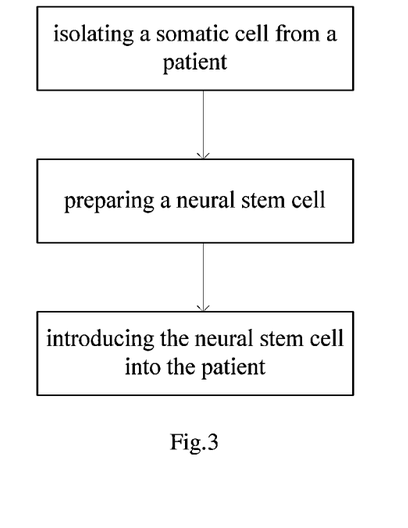
FIG. 3 is a flow chart showing a method of treating a neurodegenerative disease or a disease induced by neural cell damage according to an embodiment of the present disclosure.

Embodiments of an eleventh broad aspect of the present disclosure provide a system for preparing a neural stem cell. According to embodiments of the present disclosure, referring to FIG. 2, the system 1000 may comprise: isolating apparatus 100, transforming apparatus 200 and transdifferentiation apparatus 300. In which, the isolating apparatus 100 is used for isolating a human urine exfoliative cell from human urine. The transforming apparatus 200, connected to the isolating apparatus 100 and equipped with a vector carrying a nucleic acid sequence encoding a pluripotent stem cell factor, in which the pluripotent stem cell factor is at least one selected from a group consisting of Oct4, Sox2, Klf4 and miR302, is used for transforming the human urine exfoliative cell received from the isolating apparatus 100. The transdifferentiation apparatus 300, connected to the transforming apparatus and equipped with the medium above-mentioned, for subjecting transformed human urine exfoliative cell received from the transforming apparatus 200 to transdifferentiation, to induce transdifferentiating the transformed human urine exfoliative cell to the neural stem cell. Using the system may effectively implement the method of the preparing the neural cell above-mentioned, which may effectively prepare the neural stem cells. Embodiments of a twelfth broad aspect of the present disclosure provide a method of screening a compound for inducing differentiation of a neural stem cell. According to embodiments of the present disclosure, the method may comprise: contacting the neural stem cell above-mentioned with a candidate compound, and determining pluripotency of the neural stem cell prior to and after the step of contacting the neural stem cell with the candidate compound, respectively, wherein the decrease of the pluripotency after contacting the neural stem cell with the candidate compound is an indicator of the candidate compound having the ability of inducing differentiation of a neural stem cell. Using the method may effectively screen to obtain the compound for inducing differentiation of the neural stem cell. Embodiments of a thirteenth broad aspect of the present disclosure provide a method of treating a neurodegenerative disease or a disease induced by neural cell damage. According to embodiments of the present disclosure, referring to FIG. 3, the method may comprise following steps:

firstly, isolating a somatic cell from a patient.

secondly, preparing a neural stem cell based on the somatic cell according to the method above;

and introducing the neural stem cell into the patient.

Using the method of treating a neurodegenerative disease or a disease induced by neural cell damage, may effectively introduce obtained neural stem cells into a patient, which may further effectively differentiate to neural cells in the patient, and remedy a body damage induced by neurodegeneration and neural cell damage, which may be able to treat the neurodegenerative disease and the disease induced by neural cell damage.

Embodiments of a fourteenth broad aspect of the present disclosure provide a method of determining whether a medicament affects a nervous system. According to embodiments of the present disclosure, the method may comprise: contacting the medicament with the neural stem cell according to embodiments of the present disclosure; and determining the neural stem cell prior to and after the step of contacting the medicament with the neural stem cell, determining whether the medicament affects the nervous system based on a change of the neural stem cell. Using the method may effectively determine whether the medicament affects the nervous system.

It should note that the medium for preparing the neural stem cell and use thereof are accomplished through hard creative labor and optimal word by the inventors of the present disclosure. In addition, the characteristics described in every aspect of the present disclosure may mutually refer each other, which are omitted here for convenience.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art or in accordance with the product instructions. If the manufacturers of reagents or instruments are not specified, the reagents or instruments may be commercially available.

Example 1: Preparation of Neural Stem Cell

1. Isolating a Human Urine Exfoliative Cell (Urine Cells, UC)

Isolating urine exfoliative cell accords with following steps:

(1) collecting 150-200 mL of midstream of urine in a sterile container added with Penicillin/streptomycin;

(2) transferring the urine into a 50 mL centrifuge tube, and centrifuging at 400 g for 10 min;

(3) discarding supernatant to retain about 5 mL of the urine;

(4) adding about 10 to 30 mL of PBS containing the Penicillin/streptomycin to the urine obtained in step (3), and centrifuging at 400 g for 10 min after gently being mixed;

(5) discarding supernatant until the remained liquid less than 0.5 mL;

(6) adding 1 mL of medium for culturing urine to the remained liquid of the urine to resuspend obtained precipitate, and collecting cells;

(7) seeding the collected cells into a 60 mm culture dish (or a six-well plat) coated by 0.1% Gelatin with additional 1 mL of medium for culturing urine, in which the medium for culturing urine was obtained by equally mixing high-glucose DMEM (Dulbcco's Modified Eagle Medium, From HyClone) supplemented with 10% fetal bovine serum (FBS, From PAA) and Penicilin/streptomycin, with SingleQuot Kit CC-4127 REGM Medium (From Lonza);

(8) placing the culture dish seeded with cells in a 37° C., 5% $CO_2$ incubator for 3 days;

(9) observing whether the cell attached to bottom of the dish, and gently adding additional 1 mL of the medium for culture urine, placing the culture dish seeded with cells in the 37° C., 5% $CO_2$ incubator for continuous culture;

(10) discarding the medium in the culture dish at the $5^{th}$ to $7^{th}$ day from the day of seeding, adding fresh medium for culturing urine (without antibiotic) to the culture dish after being washed with PBS once, by which growth of adherent cell could be observed;

(11) adding or changing the medium depending on cell growth condition, which could be sub-cultured using 0.25% trypsin;

(12) harvesting the primary human urine exfoliative cells from the $2^{nd}$ generation, and freezing and storing in liquid nitrogen using a frozen liquid (90% FBS+10% DMSO) for use.

2. Inducing Induced Neural Stem Cell (iNSC)

Experiment of inducing induced neural stem cell included: cell preparation, electrical transduction of plasmid, cell seeding induction, cell clone selection, iNSC amplification and etc. In details:

(1) thawing the frozen primary human urine exfoliative cell, seeding in a 10 cm dish (or a six-well plate);

(2) digesting adherent cells using 0.25% trypsin when a confluency of the adherent primary human urine exfoliative cell became about 90% in the 10 cm dish, and then harvesting and counting digested cells;

(3) transferring the digested cells having an appropriate cell number (the cell number ranged from 500,000 to 1,500,000 in every electrical transduction system) to a 1.5 mL of EP tube, and then centrifuging at 200 g for 5 min;

(4) discarding supernatant obtained in step (3), and harvesting obtained cell precipitate into a cup of electrical transduction;

(5) preparing a plasmid transforming system: adding 82 µL of Basic Nucleofector® Solution for Mammalian Epithelial Cells and 18 µL of supplement 1 (Lonza) in sequence followed by gently mixing, and then adding 5 µg of plasmids with sufficiently mixing, to obtain the plasmid transforming system, in which the plasmids included pCEP4-O2SET2K (3 µg) and pCEP4-miR-302 (2 µg);

(6) placing the cup mentioned in the step (4) onto Amaxa electroporator (Lonza) and performing electrical transduction by selecting T-013 (or T-020) procedure; (7) transferring electrically-transduced cells into a six-well plate (or a 10 cm dish) coated with Matrigel with a seeding density of 100,000 to 300,000 cells per well, which could be adjusted depending on cell condition, and then adding the medium for culturing urine cell; (8) changing the medium for culturing urine cell by mTeSR1 medium containing 3 μM of CHIR99021, 104 of PD0325901, 0.5 μM of A83-01 (Tocris Bioscience), 0.5 μM of thiazovivin and 0.2 μM of DMH1 (Tocris Bioscience) at the second day from the seeding in the step (7) (or the second day after transfection), in which the mTeSR1 medium was the medium for preparing the neural stem cell of the present disclosure, which was used for culturing cells and changed every two days.

(9) selecting cell clone and dividing into small pieces by mechanical method, and then seeding selected cells in a six-well plate (or a twelve-well plate) coated with Matrigel, and culturing seeded cells with conventional mTeSR1 medium, in which the cell clone was obtained after 12 to 15 days from the electrical transduction, and the cell clone was in a shape with an appropriate size, a distinct edge and a compact array which was developed from electrically-transduced cells.

(10) changing fresh medium when adherent cells was observed, and culturing the adherent cells for another three to five days and changing the medium every other day, by which a large number of neural stem cell-like cell clusters arrayed in Rosette-like neural structure or polarity shape were observed. (11) selecting neural stem cell-like cell cluster by mechanical method, and gently pipetting the neural stem cell-like cell cluster with 1 mL pipette, to pipette the neural stem cell-like cell cluster into small pieces or single cells, then transferring obtained single cells into a T25 flask containing the medium for culturing neural stem cell, in which the medium for culturing neural stem cell included DMEM/F2 medium complemented with 1% N2 supplement (Gibco), 1% non-essential amino acid (NEAA, Gibco), 0.1% heparin (Sigma), 20 ng/ml basic fibroblast growth factor (bFGF, Invitrogen) and 20 ng/ml epidermal growth factor (EGF, R&D System);

(12) obtaining neural spheres with a distinct boundary from the single cells suspending cultured in the T25 flask for one week (the neural spheres herein was defined as neural spheres of P1 generation), from which the medium was changed every two or three days with half volume comparing that of the original medium.

(13) passaging the neural spheres when the single cells were cultured for 7 to 14 days and had a size of the neural spheres, namely, the $7^{th}$ to $14^{th}$ day from the day of transferring the single cells into the T25 flask and culturing with the medium for culturing the neural stem cell, selecting and transferring those neural spheres having a diameter more than 300 μm into a 15 mL of centrifuge tube, sedimentating the neural spheres or centrifuging at 50 g for 1 min or 2 min, digesting at 37° C. for 3 min to 5 min with 1 mL of Accutase after discarding obtained supernatant; (14) adding the medium for culturing neural stem cell (in which the medium for culturing neural stem cell included DMEM/F2 medium supplemented with 1% N2 supplement (Gibco), 1% non-essential amino acid (NEAA, Gibco), 0.1% heparin (Sigma), 20 ng/ml basic fibroblast growth factor (bFGF, Invitrogen) and 20 ng/ml epidermal growth factor(EGF, R&D System)) to the above centrifuge tube until reaction system therein having a volume of 10 mL, then centrifuging at 200 g for 5 min, (15) adding a small amount of a the medium for culturing stem cell (about 500 μL) after discarding obtained supernatant in the step (14) and followed by a gentle mixing, and gently pipetting the cell cluster into small pieces using 1 mL pipette, adding 1 mL of the medium for culturing neural stem cellin to the centrifuge tube, seeding obtained cells after evenly being mixed in to a new flask, to obtain the second generation of the neural sphere.

Figure 4:
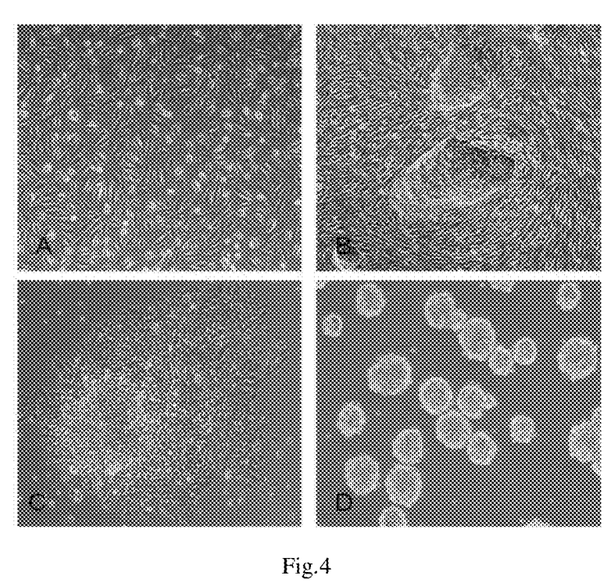
FIG. 4 is an image showing cell morphology of different phases during inducing induced neural stem cell according to an embodiment of the present disclosure.

Optionally, an inverted microscope (Olympus, BX51) was used for observing and photographing the cell morphology in different cell phases during preparing the neural stem cell by inducing from the primary human urine exfoliative cells, a result thereof could refer to FIG. 4. FIG. 4 was an image showing cell morphology of different phases during inducing induced neural stem cell according to an embodiment of the present disclosure;

As shown in the FIG. 4, A represented the primary human urine exfoliative cells; B represented cell clone induced by subjecting the cells to electrical transduction; C was a morphology of selected adherent cell clone; D was neural spheres of iNSC, the zoom factor was 100.

Example 2: Phenotype Determination of Induced Stem Cell (iNSC)

Figure 5:
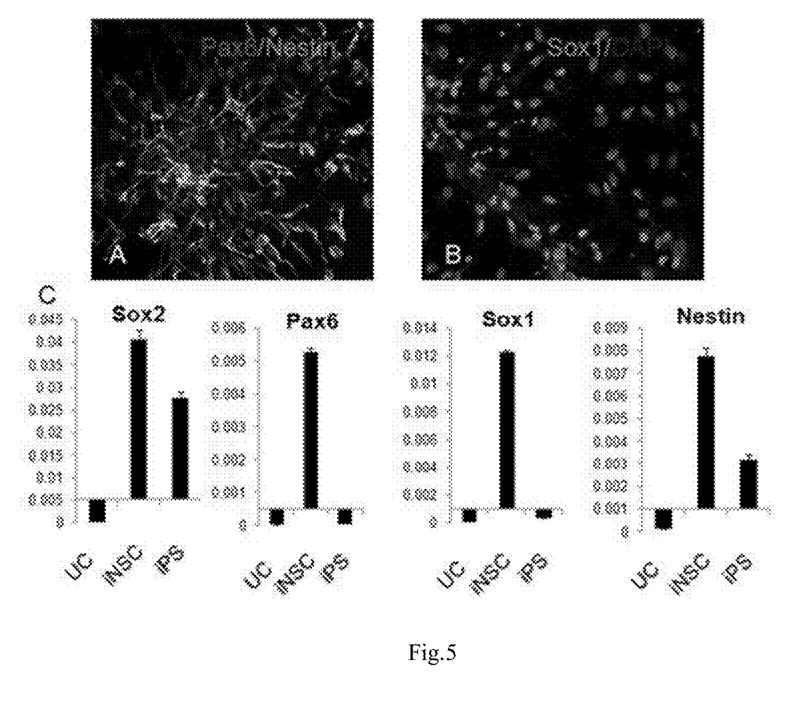
FIG. 5 is an image showing an expression level of a marker gene in neural stem cells in induced neural stem cells determined by immunofluorescence and Real-Time PCR according to an embodiment of the present disclosure.

1. Expression Determination of NSC Marker in iNSC by Immunofluorescence (1) laying a slide coated with Matrigel in a 24-well plate, attaching 5 to 10 of iNSC neural sphere having a small volume prepared in Example 1 to the slide, and then adding 100 μL of the medium for culturing the neural stem cell thereon, then adding 500 μL of the medium for culturing the neural stem cell into each well of the 24-well plate at the next day, then culturing for 1 to 2 days;

(2) allowing cultured cells obtained in the step (1) to fix for 20 min at room temperature in 4% paraformaldehyde;

(3) rinsing fixed cell three times with PBS for 5 min each time;

(4) incubating the cells obtained in the step (3) in PBS added with a primary antibody (Pax6, Nestin, Sox1 or Sox2), 1% BSA, 10% normal goat serum, 0.3% Triton-X, at 4° C. overnight;

(5) rinsing the cells obtained in the step (4) three times with PBS for 5 min each time;

(6) incubating the cells obtained in the step (5) with secondary antibody (Invitrigen) marked with Alexa 568 or 488 for 1 hr at room temperature in the dark;

(7) rinsing the cells obtained in the step (6) three times with PBS for 5 min each time;

(8) incubating the cells obtained in the step (7) withe DAPI (Sigma) for 3 min at room temperature in the dark;

(9) rinsing the cells obtained in the step (8) three times in PBS for 5 min each time;

(10) mounting the slide having the cells obtained in the step (9), and observing the samples by photograph, a result thereof could refer to FIG. 5.

2. Expression Determination of the Neural Stem Cell Marker Genes in Induced Neural Stem Cell (iNSC) by Real-Time PCR Firstly, the Trizol reagent (Takara) was used to extract total RNA of the induced neural stem cell prepared in Example 1 manual in accordance with specification provided by manufacturer. Then, M-MLV kit (Takara) was used to subject extracted total RNA to reverse transcription, to obtain cDNA, and SYBR® Premix Ex Taq kit (Takara) and ABI 7300 fluorescent quantitation PCR instrument were used to subject obtained cDNA to Real-Time PCR, to determine the expression of the neural stem cell marker genes, a result thereof could refer to FIG. 5. In which, sequences of primers in the Real-Time PCR is below.

| Primer name | Sequence of primer (SEQ ID NO: ) |
|---|---|
| PAX6-F | ATGTGTGAGTAAAATTCTGGGCA (1) |
| PAX6-R | GCTTACAACTTCTGGAGTCGCTA (2) |
| SOX1-F | CAGTACAGCCCCATCTCCAAC (3) |
| SOX1-R | GCGGGCAAGTACATGCTGA (4) |
| NESTIN-F | CTGGAGCAGGAGAAACAGG (5) |
| NESTIN-R | TGGGAGCAAAGATCCAAGAC (6) |
| SOX2-F | CCCAGCAGACTTCACATGT (7) |
| SOX2-R | CCTCCCATTTCCCTCGTTTT (8) |

Note:
F: forward;
R: reverse.

FIG. 5 was an image showing an expression level of a marker gene in neural stem cells in induced neural stem cells determined by immunofluorescence and Real-Time PCR according to an embodiment of the present disclosure As shown in FIG. 5, A and B was staining results of immunofluorescence, A indicated that expressions of both Pax6 Nestin were positive in iNSC, B indicated that expression of Sox1(B) was positive in iNSC; C was the result of Real-Time PCR detection, which respectively showed expression levels of Sox2, Pax6, Sox1 and Nestin in iNSC, in which UC represented the urine cell, iPS was pluripotent stem cell induced from the primary human urine exfoliative cell.

3. Determination of Differentiation Ability of iNSC In Vitro

The slide coated with Matrigel were laid in 24 well-plate, iNSC neural spheres prepared in Example 1 (induced neural stem cell) were attached onto the slide laid in each well of the 24 well-plate, 100 μL of the medium for culture neural stem cell was added thereon, 1 mL of a medium for neural differentiation was added in to each well of the 24-well plate at the next day, then the cells were cultured for 1 to 2 days, in which the medium for neural differentiation comprises DMEM/F2 medium supplemented with 1% N2 supplement (Gibco), 1% non-essential amino acid (NEAA, Gibco), 0.1% heparin (Sigma) and neurotrophinbasic (Peprotech), in which the neurotrophinbasic consisted of 10 ng/mL BDNF, 10 ng/mL GDNF, 10 ng/mL CNTC and 10 ng/mL IGF. The medium for culturing neural differentiation was changed every two days with half volume comparing with that of the original medium for culturing neural differentiation. Differentiated products in vitro of the induced neural stem cells were obtained after 2 weeks' culturing described above. Then, expressions of obtained differentiated products in vitro of the induced neural stem cells, such as Tuj, Map2, Dcx, TH, GABA, Glutamine and GFAP proteins, were detected by immunofluorescence, a result thereof could refer to FIG. 6. In details, TH, GABA, Glutamine and GFAP proteins were markers specific for different types of neurons and neuroglia cells, by which different types of neurons and neuroglia cells, obtained from the induced neural stem cell via in vitro differentiation, could be determined by detecting expressions of Tuj, Map2, Dex, TH, GABA, Glutamine and GFAP proteins respectively in the differentiated products in vitro of the induced neural stem cells, which may further determine in vitro differential ability of induced neural stem cells.

Figure 6:
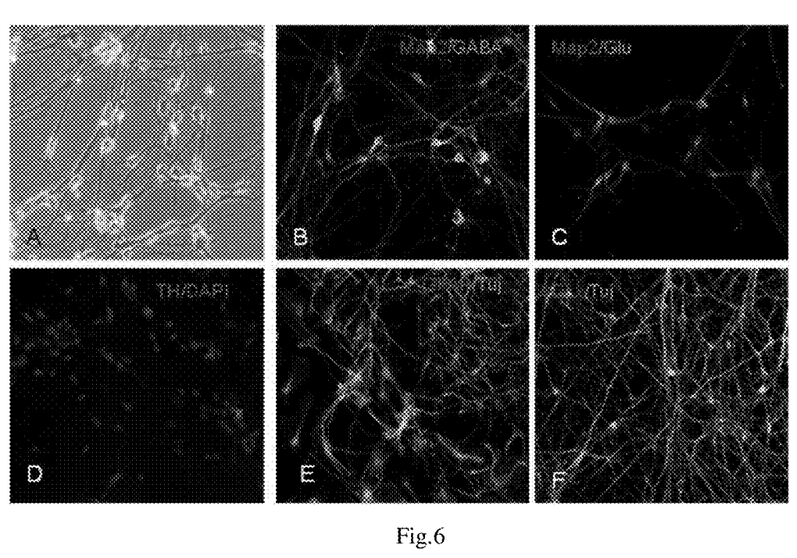
FIG. 6 is an image showing expressions of different markers specific for different types of neurons and neuroglia cells among in-vitro differentiation products deriving from induced neural stem cells determined by immunofluorescence according to an embodiment of the present disclosure.

FIG. 6 was an image showing expressions of different markers specific for different types of neurons and neuroglia cells among in-vitro differentiation products deriving from induced neural stem cells determined by immunofluorescence according to an embodiment of the present disclosure As shown in FIG. 6, A indicated that iNSC spontaneously formed into a large amount of neurons and neuroglia cells; B indicated that expressions of Map2 and GABA were positive in the differentiated products in vitro of the induced neural stem cells; C indicated that expressions of Map2 and Glutamine were positive in the differentiated products in vitro of the induced neural stem cells; D indicated that expression of TH was positive in the differentiated products in vitro of the induced neural stem cells; E indicated that expressions of Tuj and GFAP (an astrocyte marker) were positive in the differentiated products in vitro of the induced neural stem cells; F indicated that expressions of Dcx and Tuj were positive in the differentiated products in vitro of the induced neural stem cells.

INDUSTRIAL APPLICATION

A medium for preparing a neural stem cell of the present disclosure may be applied to effectively prepare the neural stem cell. Using the medium to culture a somatic cell, particularly a somatic cell expressing a transcriptional regulation factor, may effectively transdifferentiate the somatic cell to neural stem cell with greatly-shortened time.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A medium for preparing neural stem cells from urine exfoliative cells consisting of:
 a basic medium for culturing a stem cell, and
 an inhibitor; consisting of glycogen synthase kinase (GSK) inhibitor, a mitogen-activated extracellular signal-regulated kinase (MEK) inhibitor, a transforming growth factor-β (TGF-β) inhibitor, a Rho associated kinase (ROCK) inhibitor and a bone morphogenetic protein (BMP) inhibitor.

2. The medium of claim 1, wherein the basic medium is mTeSR1.

3. The medium of claim 1, wherein the inhibitor consists of a GSK inhibitor CHIR99021, a MEK inhibitor PD0325901, a TGF-β inhibitor A83-01, a ROCK inhibitor thiazovivin and a BMP inhibitor DMH1.

4. The medium of claim 1, wherein the inhibitor consists of:
 0.3 μM to 30 μM of GSK inhibitor CHIR99021,
 10 nm to 10 μM of MEK inhibitor PD0325901,
 50 nm to 5 μM of TGF-β inhibitor A83-01,
 50 nm to 5 μM of ROCK inhibitor thiazovivin, and
 20 nm to 2 μM of BMP inhibitor DMH1.

5. The medium of claim 1, wherein the inhibitor consists of:
 3 μM of GSK inhibitor CHIR99021,
 1 μM of MEK inhibitor PD0325901,
 0.5 μM of TGF-0 inhibitor A83-01,
 0.5 μM of ROCK inhibitor thiazovivin, and
 0.2 μM of BMP inhibitor DMH1.

* * * * *

SEQUENCE LISTING

<160> NUMBER OF SEQ ID NOS: 8

<210> SEQ ID NO 1
<211> LENGTH: 23
<212> TYPE: DNA

```
<213> ORGANISM: Artificial Sequence
<220> FEATURE:
<223> OTHER INFORMATION: Primer

<400> SEQUENCE: 1
atgtgtgagt aaaattctgg gca                                              23

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gcttacaact tctggagtcg cta                                              23

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
cagtacagcc ccatctccaa c                                                21

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
gcgggcaagt acatgctga                                                   19

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
ctggagcagg agaaacagg                                                   19

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tgggagcaaa gatccaagac                                                  20

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
cccagcagac ttcacatgt                                                   19
```

```
<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cctcccattt ccctcgtttt                                          20
```

UNITED STATES PATENT AND TRADEMARK OFFICE
CERTIFICATE OF CORRECTION

PATENT NO. : 10,011,819 B2
APPLICATION NO. : 14/382188
DATED : July 3, 2018
INVENTOR(S) : Guangjin Pan et al.

Page 1 of 1

It is certified that error appears in the above-identified patent and that said Letters Patent is hereby corrected as shown below:

In the Claims

Column 18, Claim 5:
Please delete "The medium of claim 1, wherein the inhibitor consists of:
3 µM of GSK inhibitor CHIR99021,
1 µM of MEK inhibitor PD0325901,
0.5 µM of TGF-0 inhibitor A83-01,
0.5 µM of ROCK inhibitor thiazovivin, and
0.2 µM of BMP inhibitor DMH1."

And insert -- The medium of claim 1, wherein the inhibitor consists of:
3 µM of GSK inhibitor CHIR99021,
1 µM of MEK inhibitor PD0325901,
0.5 µM of TGF-β inhibitor A83-01,
0.5 µM of ROCK inhibitor thiazovivin, and
0.2 µM of BMP inhibitor DMH1. --

Signed and Sealed this
Eleventh Day of December, 2018

Andrei Iancu
*Director of the United States Patent and Trademark Office*